US012758695B2

(12) United States Patent
Nageshwaran et al.

(10) Patent No.: US 12,758,695 B2
(45) Date of Patent: Oct. 13, 2026

(54) WEARABLE AUTOMATED PERITONEAL DIALYSIS DEVICE

(71) Applicants: BAXTER INTERNATIONAL INC., Deerfield, IL (US); BAXTER HEALTHCARE SA, Glattpark (CH)

(72) Inventors: A S Nageshwaran, Whitefield (IN); Brijoy Patel, Whitefield (IN); Ramkumar Jeyachandran, Whitefield (IN); Emmanuel Thomas Nishanth Irudhayaraj, Whitefield (IN)

(73) Assignees: Vantive US Healthcare LLC, Deerfield, IL (US); Vantive Heatlh GMBH, Glattpark (CH)

( * ) Notice: Subject to any disclaimer, the term of this patent is extended or adjusted under 35 U.S.C. 154(b) by 525 days.

(21) Appl. No.: 18/019,442

(22) PCT Filed: Jul. 29, 2021

(86) PCT No.: PCT/US2021/043637
§ 371 (c)(1),
(2) Date: Feb. 2, 2023

(87) PCT Pub. No.: WO2022/031506
PCT Pub. Date: Feb. 10, 2022

(65) Prior Publication Data

US 2023/0293793 A1 Sep. 21, 2023

(30) Foreign Application Priority Data

Aug. 3, 2020 (IN) ............................ 202041033188

(51) Int. Cl.
*A61M 1/28* (2006.01)
*A61M 1/14* (2006.01)
(Continued)

(52) U.S. Cl.
CPC ............ *A61M 1/281* (2014.02); *A61M 1/155* (2022.05); *A61M 1/1664* (2014.02);
(Continued)

(58) Field of Classification Search
CPC .... A61M 1/155; A61M 1/1664; A61M 1/281; A61M 2205/3334; A61M 2205/3341;
(Continued)

(56) References Cited

U.S. PATENT DOCUMENTS 3,884,808 A 5/1975 Scott
5,324,422 A * 6/1994 Colleran .............. A61M 1/288 210/85
(Continued)

FOREIGN PATENT DOCUMENTS

CN 1060394 B * 10/2018
CN 106039446 B 10/2018
(Continued)

OTHER PUBLICATIONS

English translation Chinese Patent No. 106039446 B (2018).*
(Continued)

*Primary Examiner* — John Kim
(74) *Attorney, Agent, or Firm* — K&L Gates LLP

(57) ABSTRACT

A wearable automated peritoneal dialysis ("APD") machine is disclosed herein. In an example, the APD machine includes a delivery system connected to a dialysis fluid container and a catheter connected to a peritoneal cavity of a patient. The delivery system includes a pump for pumping fresh dialysis fluid from the dialysis fluid container to the patient, and pumping used dialysis fluid from the patient to the dialysis fluid container. The delivery system also includes a control unit configured to control the pump using a flow rate measured by a flow sensor and a pressure measured by a pressure sensor. The APD machine also
(Continued)

includes a clothing item to be worn by the patient. The clothing item includes a first section to retain the dialysis fluid container, a heating element positioned adjacent to the first section for warming the fresh dialysis fluid, and a second section to retain the delivery system.

16 Claims, 12 Drawing Sheets

(51) Int. Cl.
*A61M 1/16* (2006.01)
*A41D 13/12* (2006.01)

(52) U.S. Cl.
CPC . *A41D 13/1281* (2013.01); *A61M 2205/3334* (2013.01); *A61M 2205/3341* (2013.01); *A61M 2205/3368* (2013.01); *A61M 2205/3553* (2013.01); *A61M 2205/3561* (2013.01); *A61M 2205/3576* (2013.01); *A61M 2205/583* (2013.01); *A61M 2205/584* (2013.01); *A61M 2205/8206* (2013.01); *A61M 2209/088* (2013.01)

(58) Field of Classification Search
CPC .. A61M 2205/3368; A61M 2205/3553; A61M 2205/3561; A61M 2205/3576; A61M 2205/583; A61M 2205/584; A61M 2205/8206; A61M 2209/088; A41D 13/1281
See application file for complete search history.

(56) References Cited

U.S. PATENT DOCUMENTS

| | | | |
|---|---|---|---|
| 7,128,836 | B2 | 10/2006 | De Paolis et al. |
| 10,933,183 | B2 | 3/2021 | Gura |
| 2002/0123715 | A1 | 9/2002 | Sorenson et al. |
| 2008/0051696 | A1 | 2/2008 | Curtin et al. |
| 2009/0120864 | A1 | 5/2009 | Fulkerson et al. |
| 2015/0314056 | A1 | 11/2015 | Giordano et al. |

FOREIGN PATENT DOCUMENTS

| | | | |
|---|---|---|---|
| CN | 109999245 | A | 7/2019 |
| KR | 20070108841 | A | 11/2007 |

OTHER PUBLICATIONS

English translation Chinese Patent Application No. 109999245 A (2019).*
International Preliminary Report on Patentability for International Application No. PCT/US202W43637 dated Jul. 29, 2021.

* cited by examiner

WEARABLE AUTOMATED PERITONEAL DIALYSIS DEVICE

PRIORITY CLAIM

This application is a national phase entry of PCT/US2021/043637, filed on Jul. 29, 2021, which claims priority to Indian Provisional Application No. 202041033188, filed on Aug. 3, 2020, the entire disclosures of which are incorporated by reference herein.

BACKGROUND

Due to various causes, a person's renal system can fail. Renal failure produces several physiological derangements. For instance, it is no longer possible for a person with renal failure to balance water and minerals or to excrete daily metabolic load. Additionally, toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across a semi-permeable dialyzer between the blood and an electrolyte solution, called dialysate or dialysis fluid, to cause diffusion. The diffusion occurs externally from the patient, where an extracorporeal circuit is used for removing uncleansed blood and returning cleansed blood to the patient.

Hemofiltration ("HF") is an alternative renal replacement therapy that relies on a convective transport of toxins from a patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large toxic molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Another type of kidney failure therapy is peritoneal dialysis ("PD"), which infuses a dialysis solution, also called dialysis fluid, into a patient's peritoneal cavity via a catheter. The dialysis fluid is in contact with the peritoneal membrane in the patient's peritoneal cavity. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis, and continuous flow peritoneal dialysis ("CFPD"). CAPD is a manual dialysis treatment. Here, the patient manually connects an implanted catheter to a drain to allow used or spent dialysis fluid to drain from the peritoneal cavity. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal cavity, where the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the chamber and for the transfer of waste, toxins and excess water to take place. The source may include multiple liters of dialysis fluid including several solution bags.

APD machines pump used or spent dialysate from the patient's peritoneal cavity, though the catheter, and to the drain. As with the manual process, several drain, fill and dwell cycles occur during dialysis. A "last fill" may occur at the end of the APD treatment. The last fill fluid may remain in the peritoneal cavity of the patient until the start of the next treatment, or may be manually emptied at some point during the day.

In any of the above modalities using an automated machine, the automated machine is stationary in a medical center or a patient's home. The form factor of automated machines requires a patient to be immobilized in a bed or chair for the duration of a kidney failure therapy, which can last up to eight hours. As such, a patient undergoing a kidney failure therapy cannot move from the connected automated machine, let alone, leave their house/medical center.

A need accordingly exists for a portable or mobile automated machine that performs a renal failure therapy.

SUMMARY

Example systems, methods, and apparatus are disclosed herein for a single-pass, wearable automated peritoneal dialysis ("APD") machine. The example single-pass, wearable APD machine is configured to provide a single cycle of kidney failure therapy while a patient is walking, working, driving, or otherwise partaking in life events. The single-pass, wearable APD machine may weigh less than one kilogram, not including the dialysis fluid. Such a lightweight device enables a patient to be mobile and without having to carry around bulky equipment, thereby improving the patient's quality of life.

The single-pass, wearable APD machine includes one (or a few) bags of fresh dialysis fluid. During a fill phase, the single-pass, wearable APD machine pumps the fresh dialysis fluid into a patient's peritoneal cavity. The single-pass, wearable APD machine then permits the dialysis fluid to remain in the patient's peritoneal cavity for a dwell period.

After the dwell period, the single-pass, wearable APD machine drains the dialysis fluid from the patient's peritoneal cavity back into the one (or few) bags.

In some embodiments, the single-pass, mobile APD machine is integrated into clothing that is worn by a patient. The clothing may include, for example, a jacket with an integrated heater for warming a container that contains fresh dialysis fluid for the kidney failure therapy. The clothing may also include or provide connections to a delivery system, which provides for the delivery and removal of the dialysis fluid from a patient. The delivery system includes, in some embodiments, a control unit for controlling operation of at least one pump and fluid tubing that provides a conduit or flowpath from the container to the patient via the at least one pump. The control unit and/or the fluid tubing may include or be connected to a pressure sensor and/or a flow sensor that provides feedback to the control unit for controlling operation of the pump.

In some embodiments, the control unit provides a power supply for the heater of the clothing. In other embodiments, the clothing may include a compartment for a power supply separate from the control unit. As discussed herein, the power supply may include one or more battery.

Further, in some embodiments, portions of the delivery system, including for example a pressure sensor, flow sensor, pump head, and/or tubing may be disposable. In these embodiments, to perform another pass or cycle of the kidney failure therapy, the patient simply replaces the required components and swaps the used/spent dialysis fluid container with a new fresh dialysis fluid container.

In an alternative embodiment, the single-pass, mobile APD machine is self-contained within a bag or pouch. As disclosed herein, the bag or pouch includes space for one or more dialysis fluid container, a heater, a control unit, a pump, a pressure sensor, a flow sensor, fluid tubing, and a power supply. The bag or pouch is worn by a patient so as to not impede their movement or mobility.

In light of the present disclosure and the above aspects, it is therefore an advantage of the present disclosure to provide a wearable APD machine.

It is another advantage of the present disclosure to integrate a portable APD machine into clothing or a bag that is worn by a patient for at least one cycle or pass of a kidney failure therapy.

It is yet another advantage of the present disclosure to provide an integrated heater within clothing or a bag containing a portable APD machine.

It is further advantage of the present disclosure to provide a portable APD machine that is easily connectable to a patient's catheter and dialysis fluid container while enabling a patient to move around.

Additional features and advantages are described in, and will be apparent from, the following Detailed Description and the Drawings. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiment separately. Moreover, it should be noted that the language used in the specification has been selected principally for readability and instructional purposes, and not to limit the scope of the inventive subject matter.

DETAILED DESCRIPTION

Figure 1:
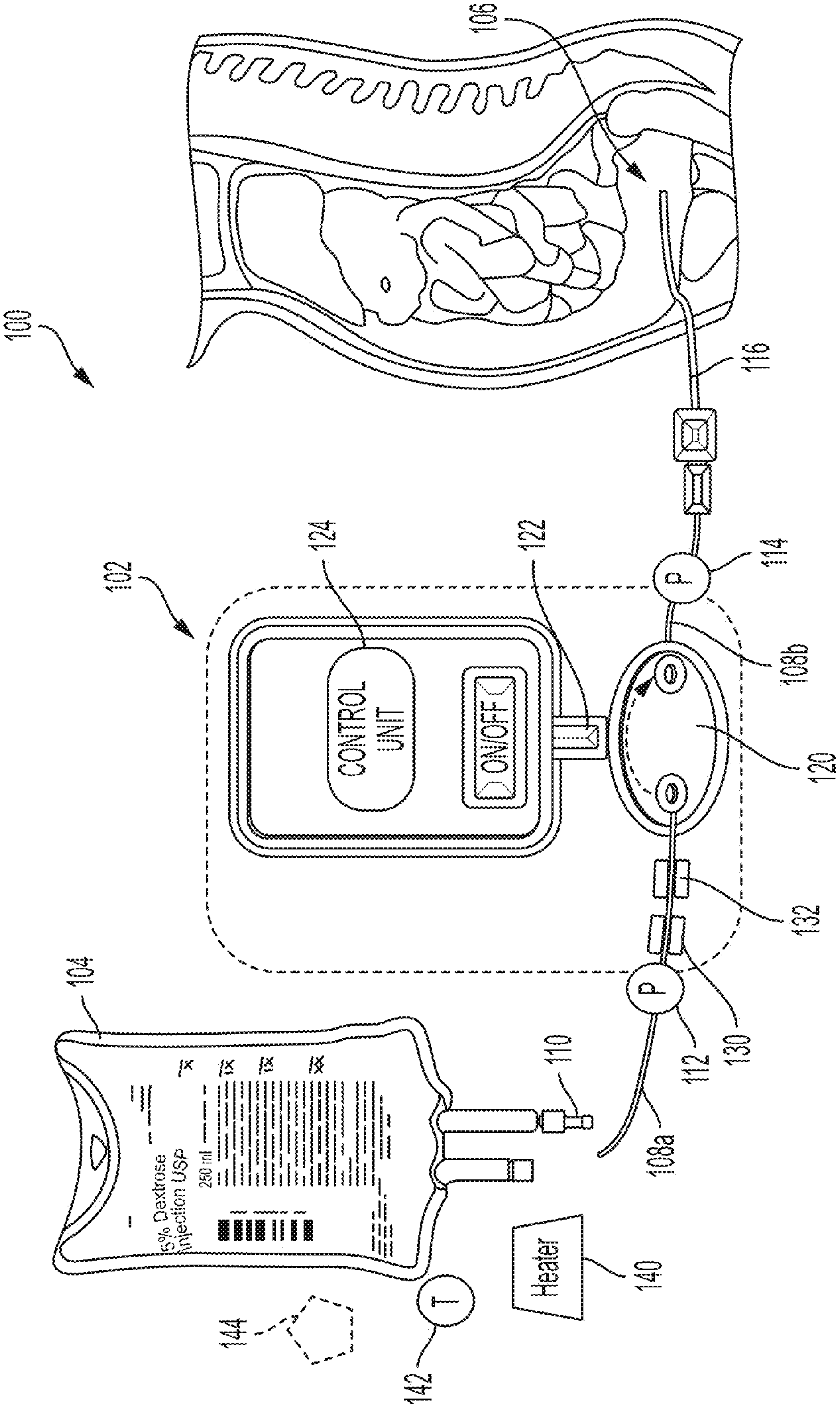
FIG. 1 is a diagram of a wearable APD machine, according to an example embodiment of the present disclosure.

Methods, systems, and apparatus are disclosed herein for a wearable APD device or machine. The example APD machine disclosed herein is configured to be mobile or portable to provide patients an on-the-go dialysis therapy. The disclosed wearable APD machine is configured to perform at least one cycle or pass of a peritoneal dialysis therapy. In some embodiments, the APD machine is integrated into patient clothing, such as a jacket, a coat, a shirt, a sweater, a tunic, or pants. In other embodiments, the wearable APD machine is integrated into a bag or pouch, which is worn by a patient.

The APD machine disclosed herein is configured to be light-weight, in some embodiments weighing less than one kilogram (without taking into account a weight of dialysis fluid in a dialysis fluid container). Additionally, the APD machine is configured to have a small size and/or low profile, which enables the machine to be worn for long durations by a patient without affecting their mobility or quality of life. The mobility of the disclosed APD machine enables patients to perform at least one cycle of a peritoneal dialysis therapy without being constrained to a bed or a chair for hours at a time.

In some embodiments, disposable components of the APD machine, such as sensors, pump head, fluid tubing, and dialysis fluid container are easily replaceable between treatments. For example, used in-line sensors, pump head, fluid tubing, and a fluid container may only have to be disconnected from a patient's catheter and a delivery system. New components may then be easily connected to the patient's catheter and delivery system for the next cycle or pass.

In some embodiments, the APD machine is configured to use only a single pump and dialysis fluid container, thereby reducing the number of components used and the overall system weight. During a fill phase of a kidney failure therapy, the pump moves fresh dialysis fluid from the fluid container into a patient's peritoneal cavity. During a dwell period (which consumes the most time during a treatment), the dialysis fluid container is substantially empty since the dialysis fluid is inside the patient, which results in less weight on the patient. After the dwell period, the same pump moves used dialysis fluid and an additional amount of ultrafiltration ("UF") removed from the patient's peritoneal cavity back into the dialysis fluid container so that a separate drain line or drain container is not needed.

The wearable APD machine is configured to operate in combination with a heater. The heater may be integrated into the patient's clothing or integrated into a bag or pouch. The heater is configured to warm fresh dialysis fluid before it can be pumped to a patient. The clothing or bag/pouch may include controls for operating the heater as well as a temperature indicator for the fresh dialysis fluid. In other instances, the heater is controlled by a control unit, which may begin pumping fresh dialysis fluid to a patient after the fluid is heated to a desired temperature (e.g., a temperature threshold), which is typically between 35° C. to 40° C., preferably around 37° C.

Reference is made herein to kidney failure therapy. The APD machine disclosed herein is configured to perform at least one cycle or pass of a kidney failure therapy, which may be part of an overall manual PD therapy or part of overall an APD therapy.

I. APD Machine Embodiments

Referring now to the drawings, FIG. 1 shows a diagram of an APD machine 100, according to an example embodiment of the present disclosure. The example APD machine 100 includes a delivery system 102 that is fluidly coupled to a dialysis fluid container 104 and a peritoneal cavity 106 of a patient. In the illustrated example, a first end of a fluid tube 108*a* (e.g., a first fluid line) is fluidly connected to a port 110 of the dialysis fluid container 104. A second end of the fluid tube 108*a* is fluidly connected to a first port 112 of the delivery system 102. In some examples, port 112 may include one or more fluid line connector.

Also as illustrated in FIG. 1, a first end of a fluid tube 108*b* (e.g., a second fluid line) is connected to a second port 114 of the delivery system 102. A second end of the fluid tube 108*b* includes a connector, which mates with a connector of a catheter 116 that provides a passageway to the patient's peritoneal cavity 106. Together, the fluid tubes 108*a* and 108*b* provide a conduit between the dialysis fluid container 104 and the peritoneal cavity 106 via the delivery system 102. Any of the tubing, fittings, hard plastic or any other disposable item discussed herein may be made of any one or more of polyvinyl chloride ("PVC"), polyethylene ("PE"), polyurethane ("PU"), polycarbonate or other non-PVC material.

The example delivery system 102 of FIG. 1 includes at least one pump head 120 that is fluidly connected to fluid tubes 108*a* and 108*b*. The pump head 120 may be disposable connected to a reusable actuator 122, which is controlled by a control unit 124. The example pump head 120 is configured to pump fresh dialysis fluid from the container 104 to the patient's peritoneal cavity 106 during a fill phase of a kidney failure therapy. The example pump head 120 is also configured to pump used dialysis fluid (including removed toxins and absorbed ultrafiltration) from the patient's peritoneal cavity 106 back to container 104 during a drain phase of a kidney failure therapy. As such, the pump head 120 (and actuator 124) are configured to operate in a forward direction (to pump fluid to a patient) and in a reverse direction (to pump fluid from the patient). In alternative embodiments, separate pumps may be used for pumping fluid to a patient and pumping or pulling fluid from a patient.

In some embodiments, the pump head 120 is configured to occlude fluid flow from the dialysis fluid container 104 until the pump head is actuated, thereby preventing free flow of dialysis fluid. The pump head 120 may occlude the dialysis fluid until (based on instructions from the control unit 124) the fluid is heated to a specified temperature and/or when the patient is ready for treatment to begin. The use of the pump head 120 for occlusion eliminates the need for a valve or line clamp, thereby reducing material weight and cost. However, in some embodiments, the dialysis system 102 may include a valve and/or the fluid tube 108 may be operable with a manual or automated line clamp.

The dialysis fluid container 104 is a dialysis fluid source and may include a bag or other enclosure configured to hold a volume of fluid, such as one to two liters. In some embodiments, dialysis fluid container 104 includes fresh, premade dialysis fluid having a certain, prescribed dextrose concentration. In some embodiments, the dialysis fluid container 104 may include two chambers, one with dialysis concentrate and another with purified water. In such embodiments, container 104 includes a seal, which when broken, enables fluid in the two chambers to mix.

The delivery system 102 of FIG. 1 also includes a pressure sensor 130 and a flow sensor 132. In some embodiments, sensors 130 and 132 are communicatively coupled to the control unit 124 via a wired interface, such as a universal serial bus ("USB") connection, or a wireless interface, such as a Bluetooth® or Zigbee® connection. In some instances, control unit 124 is configured to pair with the sensors 130 and 132 prior to operating the pump actuator 122.

Pressure sensor 130 in the illustrated embodiment is positioned to measure fluid pressure within the fluid tube 108*a*. In other embodiments, the pressure sensor 130 may be connected to or provided with the fluid tube 108*b*. The pressure measurement may be indicative of fluid pressure delivered to or removed from the peritoneal cavity 106, which may be used by the control unit 124 to ensure that pumping is performed within positive and negative pressure limits. The pressure sensor 130 may also be used by the control unit 124 for detecting a line occlusion (based on an upward positive or negative pressure spike/trend) a fluid leak (based on downward positive or negative pressure spike/trend) or a patient drain completion (based on a negative pressure increase).

The example flow sensor 132 is configured to measure a flow rate, which may be integrated at control unit 124 to determine volume of dialysis fluid flow through the fluid tube 108*b*. Data from the flow sensor 132 is used by the control unit 124 to provide volumetric accuracy control of fluid pumped by the pump head 120. In some instances, the control unit 124 is configured to track fresh dialysis fluid provided to the patient during a fill phase and used dialysis fluid pumped from the patient during a drain phrase. The control unit 124 may compare the fill and drain volumes to estimate an amount of UF removed from the patient. Control unit 124 may also estimate an amount of fluid that remains inside the peritoneal cavity 106.

In the illustrated example, the sensors 130 and 132 are shown as being in-line with the fluid tube 108*a*. It should be appreciated that the sensors 130 and 132 may be in-line with the fluid tube 108*b*. It should also be appreciated that the sensors 130 and/or 132 may include disposable tube sections that contact the fluid tube 108*b* and the dialysis fluid, while the reminder of the sensors 130 and 132 are reusable between treatments. Alternatively, the entire pressure sensor 130 may be disposable while portions of the flow sensor 132 are reusable and portions that contact the dialysis are disposable.

In some embodiments, the flow sensor 132 may be omitted. In these embodiments, the pump head 120 may include a linear or rotary pump, for example. In these instances, the control unit 124 is configured to count a number of pump strokes, and multiple the count by a pre-specified pump volume-per-stroke to determine a fluid volume delivered. The control unit 124 may also divide the fluid volume value by a pump time to determine a flowrate.

The APD machine 100 of FIG. 1 also includes a heater 140 and a temperature sensor 142 under control of and outputting respectively to control unit 124. Heater 140 is configured to heat the dialysis fluid within the container 104 to a desired temperature. The temperature sensor 142 is configured to measure a temperature of at least one of the dialysis fluid in the container 106, the container 106 itself, or an area adjacent to the container 106, depending on a placement of the sensor in an article of clothing or bag. Heater 140 may include one or more heating coils, such as heating coils included in an article of clothing. Alternatively, the heater 140 may include inductive and/or radiant heating. In some alternative embodiments, heater 140 may be part of the delivery system 102 and be configured as an in-line heater (e.g., which heats fluid flowing through a serpentine heating pathway.

In some embodiments, APD machine 100 also includes a temperature indicator 144. The temperature indicator 144 may be electrically connected to the temperature sensor 142 and display information indicative of the dialysis fluid temperature. In an example, the temperature indicator 144 may include a screen that displays a numeric value or color that is indicative of a temperature measured by the sensor 142. In other examples, the indicator 144 includes a temperature sensor (sensor 142 is integrated therein). For instance, the sensor 142/indicator 144 may include a thermochromic ink or gel that changes color based on a detected temperature. The indicator 144 is integrated on an outside of the clothing or bag to be readily visible by a patient. The use of a thermochromic ink or gel for the indicator 144 eliminates the need for a separate temperature sensor 142, thereby reducing weight, components and cost for APD machine 100.

Figure 2:
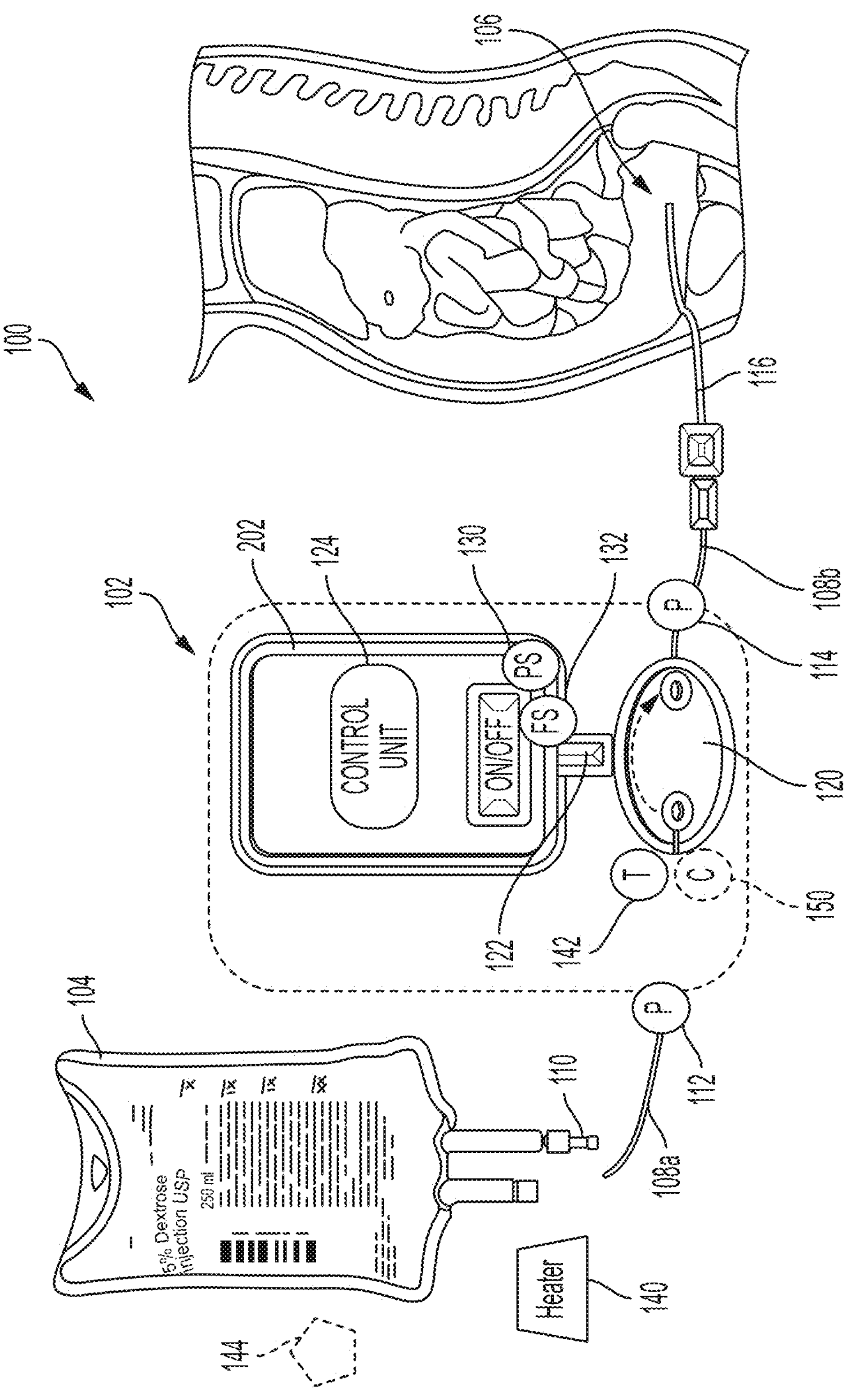
FIG. 2 is a diagram of a wearable APD machine, according to another example embodiment of the present disclosure.

FIG. 2 illustrates a diagram of another example of the APD machine 100, according to an example embodiment of the present disclosure. In the example of FIG. 1, sensors 130 and 132 are illustrated as in-line sensors. In the example of FIG. 2, the pressure sensor (PS) 130 and flow sensor (FS) 132 are contactless sensors that may be integrated with a housing 202 of the control unit 124. In other instances, the one or both of the sensors 130 and 132 (or disposable fluid-contacting portions of the sensors 130 and 132) may be integrated with the pump head 120.

Additionally, as illustrated in FIG. 2, temperature sensor 142 is included with the delivery system 102. The temperature sensor 142 may be configured as an in-line temperature sensor or as a contactless temperature sensor. In such examples, the temperature sensor 142 is communicatively coupled to the control unit 124, which enables the control unit 124 to control dialysis fluid flow based on measured temperature.

In some embodiments, delivery system 102 includes a conductivity sensor 150 that is provided in connection with the fluid tube 108*a*. A second conductivity sensor maybe provided in connection with fluid tube 108*b*. The conductivity sensor 150 may be an in-line sensor or a contactless sensor. The conductivity sensor 150 is configured to sense the conductivity of both fresh dialysis fluid (traveling to the patient) and used dialysis fluid (traveling from the patient). Sensor 150 is communicatively coupled to the control unit 124, which analyzes the measurements. For example, the conductivity sensor 150 is used to sense fresh dialysis fluid, where the control unit uses the sensor measurements to ensure the dialysis fluid is the proper type or blend. Additionally, the conductivity sensor 150 is used to sense used dialysis fluid, which enables the control unit 124 to identify or detect a solute removal level in a patient's effluent (e.g., for detection of urea, $\beta_2$ microglobulin, and/or creatinine) or for signs of peritonitis. The flowpath of the delivery system 102 is configured such that a single conductivity sensor 150 is able to perform both fresh and used dialysis fluid measurements. The conductivity sensor 150, in one embodiment, is placed adjacent to the temperature sensor 142 to enable the control unit 124 to provide temperature compensation using temperature measurements from the sensor 142.

Although not illustrated, an airtrap may be provided in the fluid tube 108*a* or the fluid tube 108*b* to remove air from the fresh dialysis fluid prior to patient delivery. Heating dialysis fluid tends to separate dissolved air from the dialysis fluid. It is accordingly contemplated to locate the airtrap downstream from the heater 140, e.g., along fluid tube 108*a* and upstream of the temperature sensor 142.

II. APD MACHINE COMPONENT EMBODIMENTS

Figure 3:
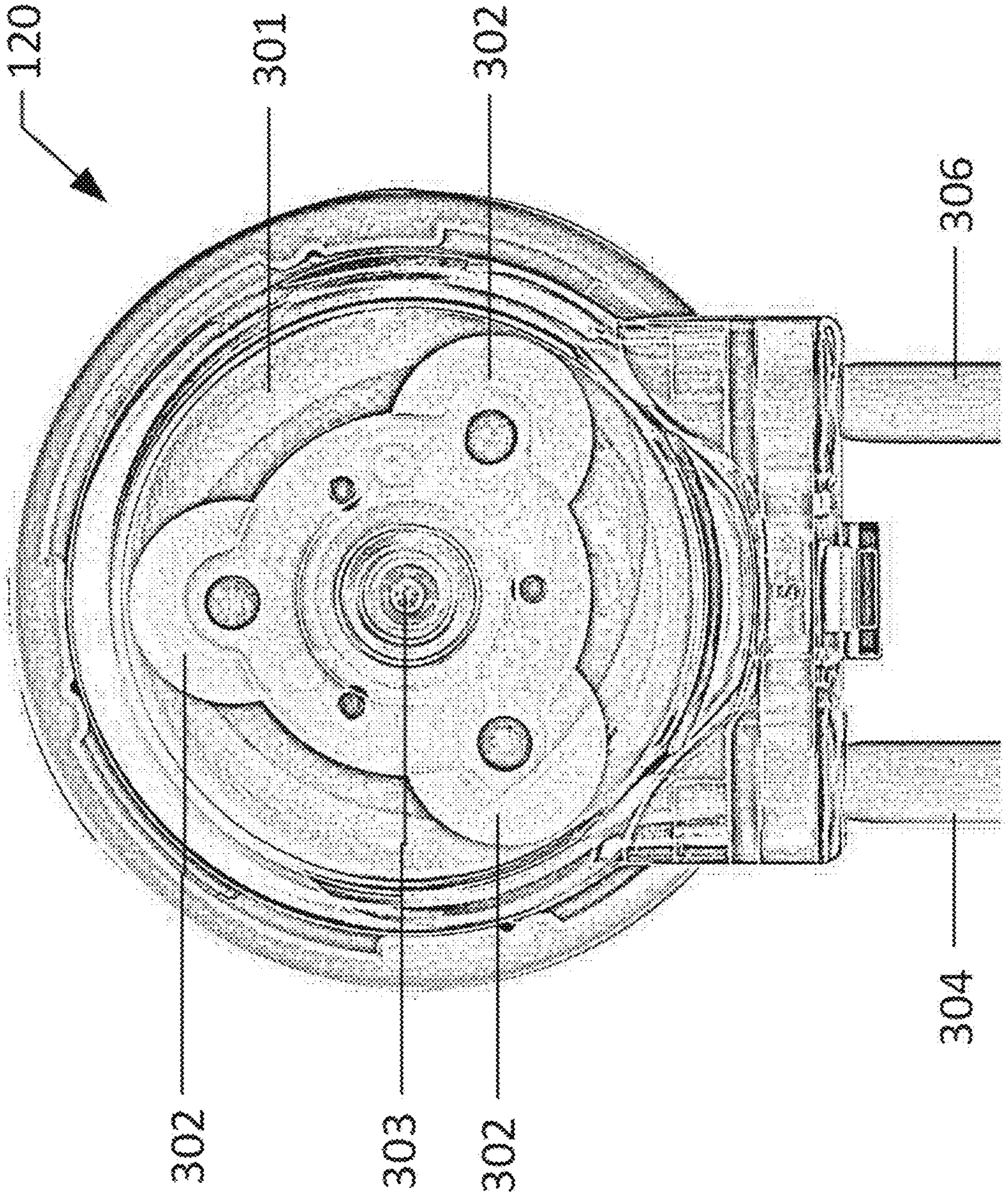
FIG. 3 is a plan view of an example pump head for the wearable APD machine of FIGS. 1 and 2, according to an example embodiment of the present disclosure.
Figure 4:
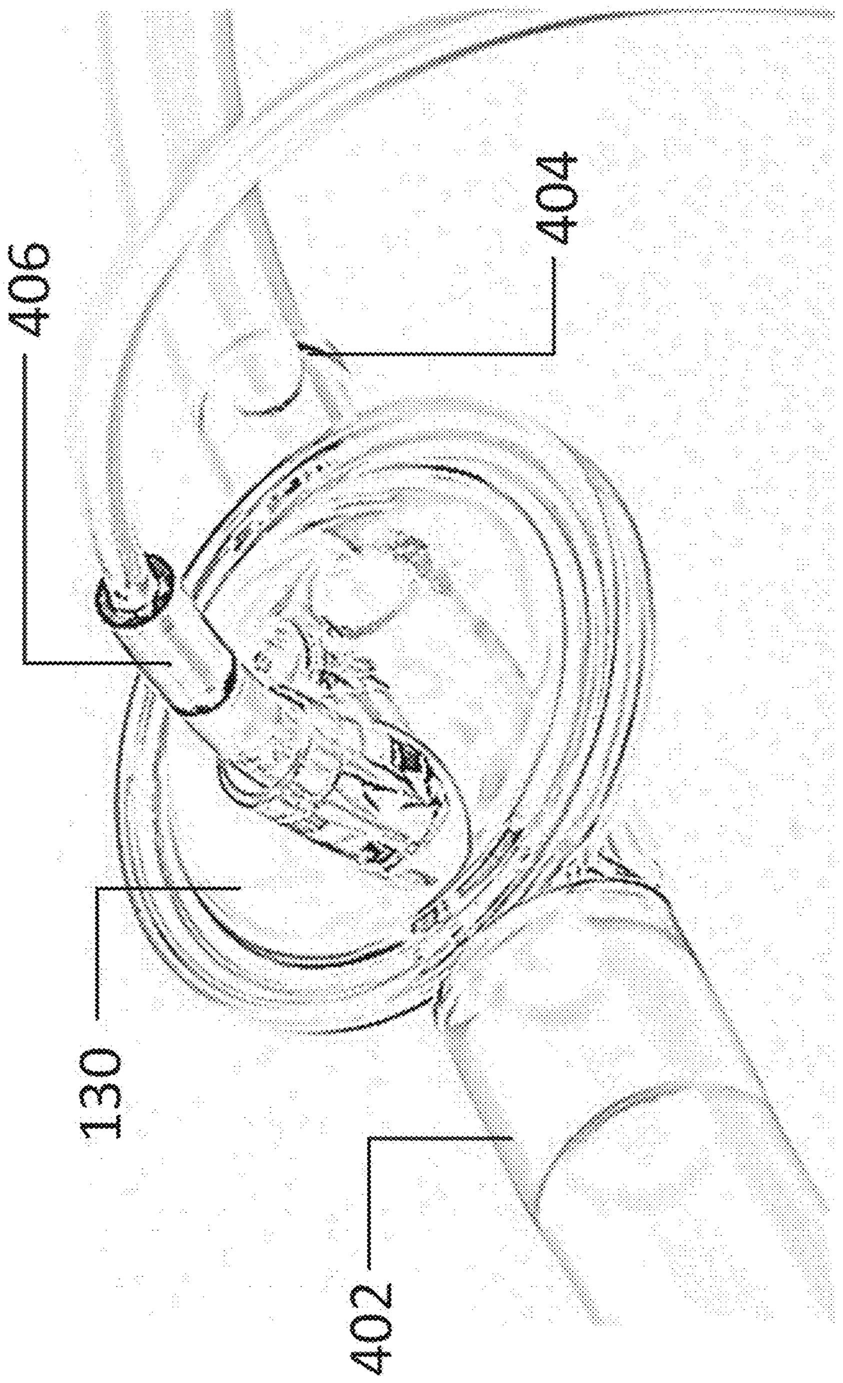
FIG. 4 is a perspective view of an example pressure sensor for the wearable APD machine of FIGS. 1 and 2, according to an example embodiment of the present disclosure.
Figure 5:
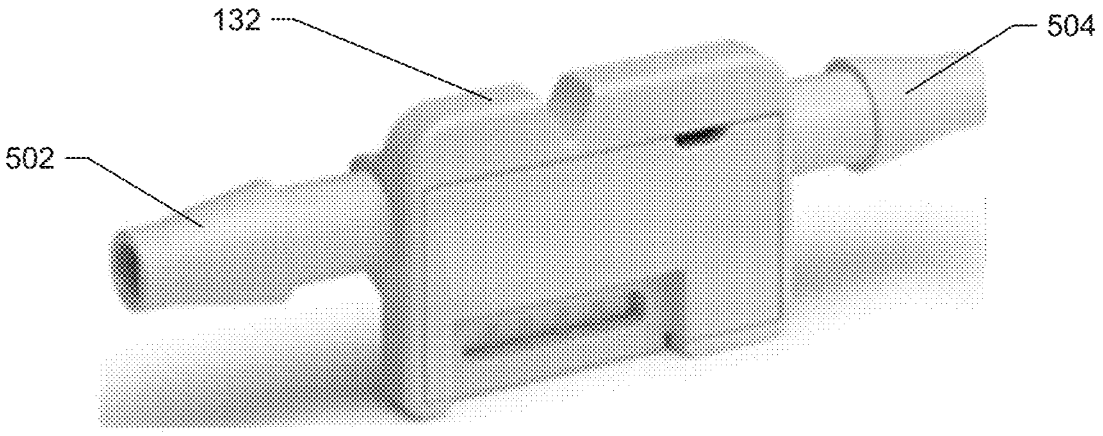
FIG. 5 is a perspective view of an example flow sensor of the wearable APD machine of FIGS. 1 and 2, according to an example embodiment of the present disclosure.

FIGS. 3 to 5 illustrate example embodiments respectively of pump head 120, pressure sensor 130, and flow sensor 132 of FIGS. 1 and 2, according to example embodiments of the present disclosure. FIG. 3 is a drawing of pump head 120, which is shown as a rotary peristaltic pump having rollers 302. Rollers 302 press against a flexible tube 301 located within pump head. The rollers are spun by a roller driver 303 around a central axis through driver 303, pushing fluid between rollers 302 in the direction in which driver 303 is spun. Pump head 120 may be bidirectional and pump dialysis fluid either way between ports 304 and 306.

In some embodiments, the pump head 120 is disposable. Here, fluid tubes 108*a* and 108*b* may be permanently connected to the ports 304 and 306, respectively, to reduce a number of potential leak points. In these instances, the pump head 120 and the tubes 108*a* and 108*b* may be removable from the delivery system 102 as a unit. In other embodiments, first port 304 may be connected to the fluid tube 108*a* and a second port 306 may be connected to the fluid tube 108*b* for easy replacement. Pump actuator 122 driving pump head 120 is reusable and under control of control unit 124 to spin in a desired direction and at a desired speed.

The pump actuator 122 causes the pump head 120 to rotate, which causes the rollers 302 to be moved in a clockwise or counterclockwise direction. Rotation of the rollers 302 causes fluid located between the rollers 302 to be moved from the first port 304 to the second port 306 via tube 301 for fluid delivery to the patient, or vice versa for a patient drain. The speed and direction of the rotation of the rollers 302 is controlled via the actuator 122 and control unit 124 as mentioned above.

Pump actuator 122 may include a stepper motor or a micro-stepper motor that is controlled by analog or digital signals from the control unit 124. For analog signals, a signal amplitude or duty cycle may be used for controlling a rotation speed of the pump actuator 122, which controls the rotation speed of the rollers 302. For digital signals, the digital value of the data transmitted to the actuator 122 is used to control rotation.

It should be appreciated that in other embodiments, the pump actuator 122 and the pump head 120 may be any type of fluid pump, such as a gear pump or a membrane pump. Additionally, the pump actuator 122 and the pump head 120 may be peristaltic pumps that operate directly with tube 108*a*. In these examples, the tube 108*a* may be inserted into the pump head 120 for use, and removed after use and replaced with a new, clean tube 108 for a next cycle. As such, the pump head 120 may not be disposable, and in some instances, integrated with the housing 202 where only a receiving portion of the tube 108*a* is exposed.

FIG. 4 illustrates an example of pressure sensor 130 of FIGS. 1 and 2, according to an example embodiment of the present disclosure. Pressure sensor 130 of the illustrated example includes a pressure pod having ports 402 and 404 for in-line connection to fluid tube 108*b*. Pressure sensor 130 is, e.g., pneumatically connected to a transducer within the housing 202 and/or the control unit 124 for sensing a pressure in the pod. In other embodiments, the pod may interface directly with the transducer.

Similar to pump head 120, pressure sensor 130 of FIG. 4 is configured to be disposable. For use, a patient connects different sections of the patient tube 108*b* to the ports 402 and 404. Additionally, a pneumatic tube from the housing 202 is connected and port 406. In some embodiments, the pressure sensor 130 may be integrated with the tube 108*b* so that it is removable from delivery system 102 as a unit (which may also include the pump head 120).

The output of pressure sensor 130 is used by the control unit 124 to ensure that (i) a positive pressure of fresh dialysis fluid delivered to the patient is within an allowable limit (e.g., 3.0 psig or less), and (ii) the negative pressure of used dialysis fluid removed from the patient is within an allowable limit (e.g., at or between −1.5 psig and zero psig). Output data from the pressure sensor 130 may also be used by the control unit 124 for detecting line occlusions, fluid leaks and/or a patient empty condition. As illustrated in FIGS. 1 and 2, flowpath of delivery system 102 is configured such that a single pressure sensor 130 is able to perform both fresh and used dialysis fluid measurements. Additional pressure sensors may be provided in the flowpath of delivery system 102 (e.g., along the fluid tube 108*a*) as desired.

FIG. 5 illustrates a flow sensor 132 of FIGS. 1 and 2, according to an example embodiment of the present disclosure. Flow sensor 132 includes ports 502 and 504 for connection to sections of the fluid tube 108*b*. In some embodiments, the flow sensor 132 may be integrated with the tube 108*b* so that they are removable from the delivery system 102 as a unit (which may also include the pump head 120 and/or the pressure sensor 130). Flow sensor 132 may be wirelessly coupled to the control unit 124 in these embodiments.

The illustrated in-line flow sensor 132 may include rotary vane, vortex shedding, magnetic, or mass flow transducers configured to measure a fluid flow rate or volume. If the flow sensor 132 is contactless, the sensor may include a heat pulse sensor, a time or flight sensor, or an optical flow sensor, for example. Output data provided by the flow sensor 132 is used by the control unit 124 as feedback for controlling the pump actuator 122 at a desired or specified flowrate. The output data from flow sensor 132 may also integrated over time by control unit 124 to yield, for example, (i) how much fresh dialysis fluid is delivered to a patient, (ii) how much used dialysis fluid is removed from a patient, and (iii) a difference between (ii) versus (i) to know how much ultrafiltration ("UF") or excess water has been removed from the patient. Output data from the flow sensor 132 may also be used by the control unit 124 for detecting line occlusions, fluid leaks and/or patient empty conditions. For example, lack of fluid flow while the pump head 120 is rotating may be indicative of a fluid leak, a tube occlusion, or an empty container 104.

III. APD MACHINE CONTROL EMBODIMENT

Figure 6:
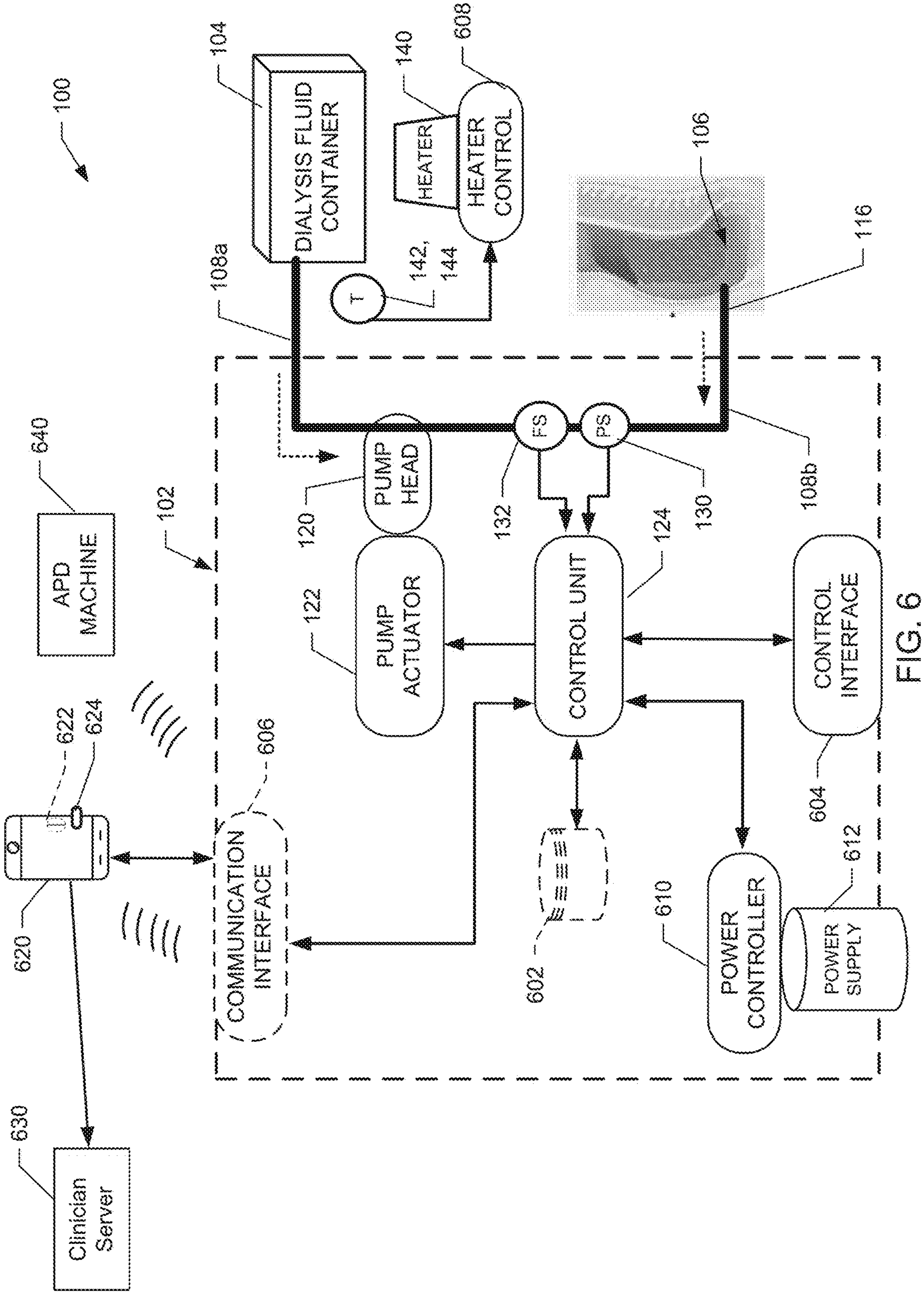
FIG. 6 is a diagram illustrating one embodiment for controlling the APD machine of FIGS. 1 and 2, according to an example embodiment of the present disclosure.

FIG. 6 illustrates a control of the APD machine 100 of FIGS. 1 and 2, according to an example embodiment of the present disclosure. In the illustrated embodiment, similar to FIGS. 1 and 2, a dialysis fluid container 104 is fluidly connected to delivery system 102, which comprises in part a fluid tube 108*a* that is fluidly connected to a pump head 120. Additionally, delivery system 102 includes a fluid tube 108*b* that fluidly connects the pump head 120 with a catheter 116, which leads to a patient's peritoneal cavity 106. In this example, a pressure sensor 130 and a flow sensor 132 of the delivery system 102 are connected in-line with the fluid tube 108*b*.

As shown, a delivery system 102 includes a control unit 124 and a memory device 602. The control unit 124 may include any processor, controller, microcontroller, logic controller, application specific integrated circuit, etc. The memory unit 602 includes programs, algorithms, or routines that are defined by a series of computer instructions, which when executed by the control unit 124, cause the control unit 124 to perform the operations described herein. The memory device may include a computer-readable medium such as random access memory ("RAM"), read only memory ("ROM"), flash memory, magnetic or optical disks, optical memory, or other storage media.

The example control unit 124 is configured to provide one or more signal to cause pump actuator 122 to rotate or otherwise provide movement for the pump head 120. The control unit 124 receives output data from the pressure sensor 130 and the flow sensor 132 for controlling the pump actuator 122. In an example, the control unit 124 may perform a fill phase of a kidney failure therapy by first pumping fresh dialysis fluid from the container 104 at a rate of 50 milliliters ("mL") per minute until 200 mL has been pumped to the patient. Then, the control unit 124 causes the pump actuator 122 to pump 800 mL of the fresh dialysis fluid at a rate of 200 mL per minute. The control unit 124 uses output data from the flow sensor 132 to calculate or determine how much fluid has been pumped to determine when to change the flow rate.

In some embodiments, the control unit 124 is communicatively coupled to the flow sensor 132 and/or the pressure sensor 130 via a wired or wireless connection. In these instances, the control unit 124 may include a transceiver configured for communication via at least one of Bluetooth®, Bluetooth® mesh, Bluetooth® low energy, Bluetooth® 5.0, Zigbee®, Z-Wave®, WeMo®, and/or LoRa. For each treatment, the control unit 124 may pair with the sensors 130 and/or 132. In some embodiments, the control unit 124 is pneumatically connected to the pressure sensor 130. In these embodiments, control unit 124 includes a transducer for detecting a change in pneumatic pressure, which is indicative of fluid pressure in the fluid tube 108*a* and/or 108*b*.

Alternatively, as discussed above in connection with FIG. 2, at least one of the sensors 130 and/or 132 are included within a housing with the control unit 124. In these instances, the sensors 130 and/or 132 may be hardwired to the control unit 124. For contact-based sensors, at least a portion of the sensor that contacts the dialysis fluid may be removable.

In some embodiments, the control unit 124 is configured to stop or pause pumping if one or more conditions are detected, such as a fluid leak, line occlusion, or an empty peritoneal cavity 106. The control unit 124 receives output data from the pressure sensor 130 and/or the flow sensor 132 that are indicative of the conditions. For example, a high fluid pressure and a low or no flow rate is indicative of a line occlusion, while a low or no fluid pressure and/or a low or no flow rate may be indicative of a leak. In another example, a high negative fluid pressure and a normal or trending lower flow rate may be indicative that the peritoneal cavity 106 is close to becoming empty.

If one or more of the above conditions are met, the example control unit 124 is configured to stop or pause the pump actuator 122. Further, the control unit 124 may use a control interface 604 to provide an indication of an alarm or an alert. The indication may include an audio indication provided by a speaker of the control interface 604 and/or a visual indication that is provided by a display screen and/or LED indicator of the control interface 604. The audio and/or visual indication may include instructions for a patient to address the detected issue, such as un-crimping a fluid tube to remove an occlusion or checking for fluid leaks. The example control unit 124 may also store information indicative of the alarm, alert, and/or event to a log stored in the memory device 602.

The control unit 124 may also store to the log of the memory device 602 medical device event information that relates to administration of a single-pass treatment. The event information may include data that is indicative of measured, detected, or determined parameter values. The control unit 124 monitors how a treatment is administered and accordingly provides parameters that are indicative of the operation. The parameters for the treatment data may include, for example, a total amount of dialysis fluid administered to the patient, dialysis fluid flowrate, dialysis dose, used dialysis fluid for effluent flowrate, dialysis fluid temperature, a number of cycles operated, a fill amount per cycle, a dwell time per cycle, a drain time/amount per cycle, an estimated amount of UF removed, a treatment start time/date, and/or a treatment end time/date. The treatment data used by the control unit 124 may be prescribed or calculated, for example, calculated as a fill rate and a drain rate determined by dividing the amount of fluid pumped by the time spent pumping. The treatment/event data may further include an identification of an alarm that occurred during a treatment, a duration of the alarm, a time of the alarm, an event associated with the alarm, and/or an indication as to whether the issue that caused the alarm was resolved or whether the alarm was silenced.

In some embodiments, the control unit 124 is configured to store medical device event information to the log of the memory device 602 over separate cycles. As such, the control unit 124 may receive a treatment plan or prescription that comprises five separate cycles. The control unit 124 monitors fluid filled and removed to determine, for example, fluid trends and/or an amount of fluid accumulation in a patient. The control unit 124 may determine for later cycles that less fresh dialysis fluid from the container 104 is to be used for fill phase and/or that less time (such as 30 minutes rather than 45 minutes) is to be used for a dwell time.

For multiple cycles that occur over the same day or over a few days, the control unit 124 may instruct the patient to change only the container 104 between each treatment such that the used dialysis fluid is replaced with fresh dialysis fluid for the next cycle. In some embodiments, the control unit 124 may additionally instruct the patient to replace disposable components, such as the pump head 120 and disposable portions of sensors between treatments. In these embodiments, the control unit 124 monitors therapy progress for each cycle.

As mentioned above, control unit 124 may operate according to programmed treatment information or a prescription. In some embodiments, the treatment information is entered via the control interface 604, which may include one or more buttons, knobs, a touchscreen, etc. The control interface 604 may include a graphical interface that enables a patient to specify, for example, treatment parameters that define how the control unit 124 is to operate to administer a treatment to a patient. For a peritoneal dialysis therapy, the parameters may specify an amount (or rate) of fresh dialysis fluid to be pumped into a peritoneal cavity of a patient, an amount of time the fluid is to remain in the patient's peritoneal cavity (i.e., a dwell time), and an amount (or rate) of used dialysis fluid and ultrafiltration ("UF") that is to be pumped or drained from the patient after the dwell period expires. For a treatment with multiple cycles, the parameters may specify the fill, dwell, and drain amounts for each cycle and the total number of cycles to be performed during the course of a treatment (where one treatment is provided per day or separate treatments are provided during the daytime and during nighttime). In addition, the parameters may specify dates/times/days (e.g., a schedule) in which treatments are to be administered by the medical fluid delivery machine. Further, parameters of a prescribed therapy may specify a total volume of dialysis fluid to be administered for each treatment in addition to a concentration level of the dialysis fluid, such as a dextrose level.

In some embodiments, the control interface 604 in connection with the control unit 124 may display a status of a treatment, including a fill rate, a dwell time (or countdown to an end of a dwell time) and a fluid removal rate. The control interface 604 may also display sequential instructions for connecting the fluid tubes 108*a* and 108*b* and any disposable components 120, 130, 132, etc. Further, as mentioned above, the control interface 604 may display alarms, alerts, and information that is indicative of events.

In addition to above, the control interface 604 may include controls for starting, pausing, and/or stopping a treatment or the pump actuator 122. In an example, the treatment cannot begin until a patient selects a start button on the control interface 604. After a treatment has begun, a patient may select a pause or stop button on the control interface 604, which causes the control unit to stop the pump actuator 122. This enables a patient to pause or stop a dialysis fluid fill of the peritoneal cavity 106 or a drain of the peritoneal cavity 106. This also enables a patient to prematurely drain the dialysis fluid before a dwell duration has elapsed.

Further, the control interface 604 may also include controls for initiating a priming sequence. For instance, after connecting the fluid tubes 108*a* and 108*b* to the container 104, activation of a priming input on the control interface 604 causes the control unit 124 to operate the pump actuator 122 to pump a small amount of fluid so as to push and remove air from the fluid tubes 108*a* and 108*b*. The control unit 124 may use output data from the flow sensor 132 to determine when the pumping should be stopped. The priming may occur before fresh dialysis fluid is heated or after the fluid is heated.

In some embodiments, at least some of the treatment information or parameters may be received in the control unit 124 from a remote source. In such embodiments, the delivery system 102 includes a communication interface 606. The example communication interface 606 is configured to provide a wired and/or wireless connection with a user device 620, such as a tablet computer or a smartphone. The connection may be made via a Wi-Fi connection, a Bluetooth® connection, a universal serial bus ("USB") connection, or any other wireless connection disclosed herein.

In some embodiments, the communication interface 606 is in communication with an APD machine 640 that is configured to perform multiple cycles. In these embodiments, the APD machine 640 may be programmed with an APD therapy comprising, for example, five cycles that are performed every two or three days. In these embodiments, the control unit 124 transmits to the APD machine 640 information that is indicative of a treatment performed, such as fill volume, drain volume, dwell duration, time/date of treatment, etc. The APD machine 640 receives the information from the control unit 124 via the communication interface 606 and logs the treatment as being performed. The APD machine 640 may also take into account the treatment performed by the APD machine 100 when preparing a treatment. For example, if a patient performs a single cycle treatment on the APD machine 100 during the day, the APD machine 640 may remove one cycle from a night treatment such that only four cycles are operated. In other examples, the APD machine 640 may make an adjustment based on fill/drain volume and an estimated volume of fluid remaining in the patient's peritoneal chamber.

The communication interface 606 is configured to receive a prescription or treatment information from the user device 620, which may include an application 622 operating on a processor 624. The application 622 is configured to connect to the communication interface 606 for transmitting the prescription or treatment information. The user device 602 may receive the prescription or treatment information from a clinician server 630.

The communication interface 606 is also configured, in some embodiments, to transmit log data from the memory device 602. The communication interface 606 may transmit the data during a treatment, after a treatment, or at periodic intervals, such as every hour. The application 622 on the user device 620 may display at least some of the log data (especially in instances where the control interface 604 has a limited display screen or no display screen). The application 622 may display, for example, a status of a treatment, including specified and/or measured treatment parameters including fill rate, dwell time, and drain amount. The application 622 may also create trends of the treatment parameters for multiple cycles of a prescription or plan. In addition, the application 622 may display alarms, alerts, and/or events that are generated by the control unit 124. In some instances, the application 622 may display instructions for replacing the disposable components 108*a* 108*b*, 120, 130, and/or 132 after each cycle.

In some instances, the application 622 may include a control interface that performs the operations described in connection with the control interface 604. For example, a patient may start a treatment using their user device 620 by selecting a start icon displayed by application 622. Such configuration eliminates the need for the control interface 604 on the delivery system 102 and enables remote control via the user device 620.

Figure 7:
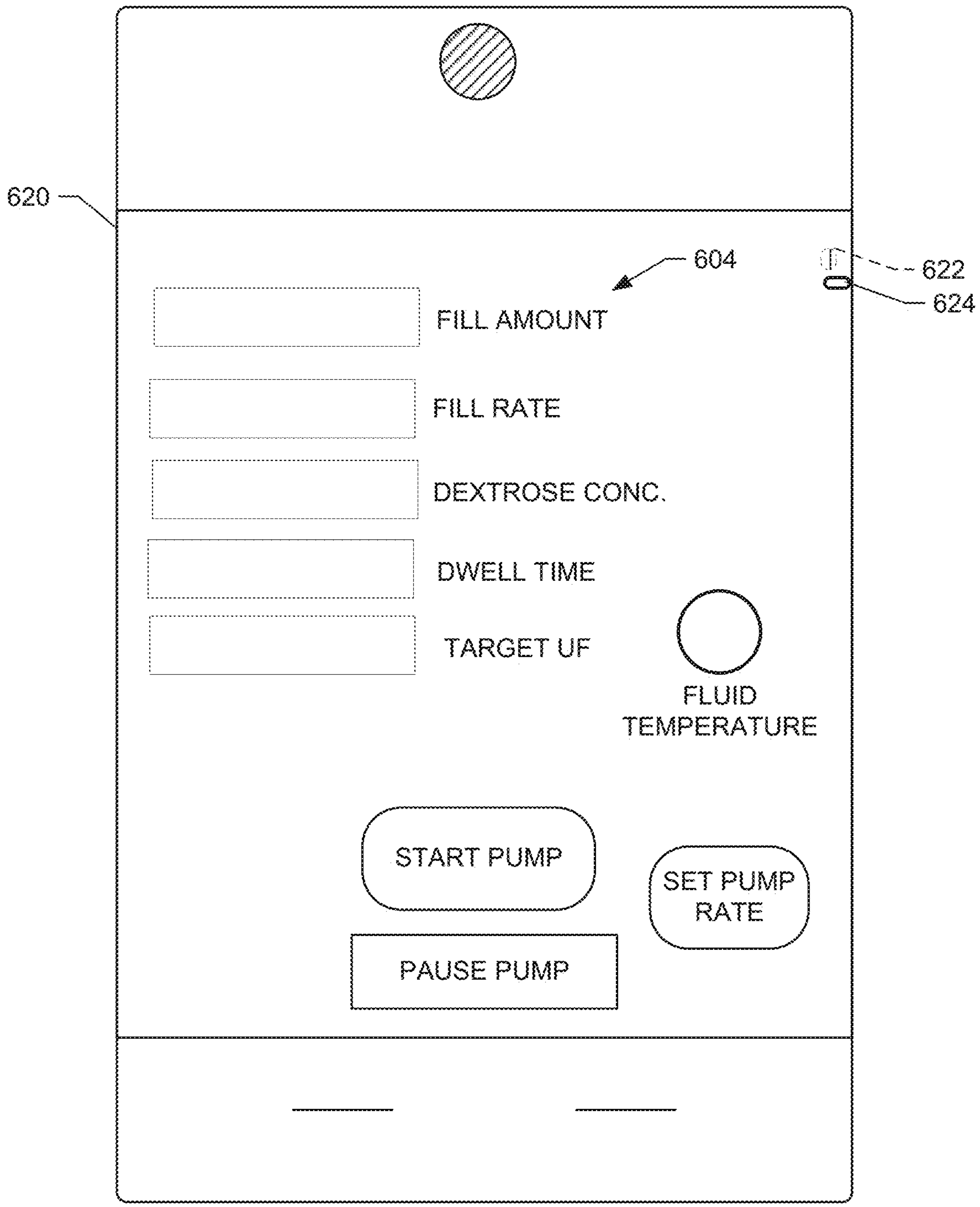
FIG. 7 is a diagram of a control interface of the APD machine of FIG. 1 or 2, or an interface of an application on a user device, according to an example embodiment of the present disclosure.

FIG. 7 illustrates control interface 604 of the delivery system 102 or an interface of the application 622, according to an example embodiment of the present disclosure. As illustrated in FIG. 7, the control interface 604 and/or the application 622 includes a field for a patient to enter at least one of a fresh dialysis fluid fill amount, a fill rate, a dextrose concentration of the dialysis fluid, a dwell time, and/or a target UF removal amount. It should be appreciated that the control interface 604 and/or the application 622 may include additional or fewer fields. The control interface 604 and/or the application 622 also includes an indicator (numeric or color-coded) for temperature, in instances where the temperature sensor 142 is communicatively coupled to the control unit 124 and/or the user device 620. The control interface 604 and/or the application 622 further includes controls for operating the pump actuator 122, such as a start command, a stop command, and a rate command.

Returning to FIG. 6, the application 622 on the user device 620 may also transmit log data to the clinician server 630. The transmission of the log data enables the clinician server 630 to track patient therapies and patient use of the APD machine 100. The log data also enables trends to be calculated to determine at the clinician server 630 if new (or modifications to) treatment parameters or a prescription is needed, which may be transmitted to the control unit 124 via the communication interface 606. Further, the transmission of the log data enables the clinician server 630 to determine if the APD machine 100 may need servicing and/or if the patient may need assistance in performing treatments.

The APD machine 100 of FIG. 6 also includes a heating system including a heater 140 and a temperature sensor 142, and/or a temperature indicator 144. In some embodiments, the heater system also includes a heater control 608, which provides control of the heater 140. As described above, the heater 140 includes heating elements or a heating pad that is built into or otherwise integrated into clothing or a bag. The heater 140 may be placed adjacent to or within a pocket or fastener used for securing the dialysis fluid container 104 in place.

In an embodiment, the heater control 608 may be started by a patient and cause a heater 140 to heat the dialysis fluid container 104 for a predetermined time that corresponds to an amount of time needed to heat one to two liters of dialysis fluid to a threshold temperature, such as 37° C. (e.g., body temperature). Temperature sensor 142 and/or indicator 144 is/are configured to measure a temperature of the dialysis fluid container and/or a temperature of the fluid itself and display an indication of the measurement. A patient may read the indicator 144 to determine when, for example, the control interface 604 is to be engaged to cause the control unit 124 to begin the pump actuator 122. Alternatively, control unit prevents actuator 122 from operation until patient temperature is reached.

In yet another alternative embodiment, temperature sensor 142 is communicatively coupled to the heater control 608. In these embodiments, the heater control 608 uses measurements of the temperature sensor 142 as feedback control to heat and maintain a temperature of the dialysis fluid container 104 at a threshold temperature until an input is received to stop heating. In further embodiments, heater control 608 is communicatively coupled to the control unit 124 or integrated with the control unit 124. Here, a patient uses the control interface 604 to cause heater 140 to warm the dialysis fluid container 104. The control unit 124 provides feedback control to maintain a temperature at a threshold level until a patient provides another input via the control interface 604 that a treatment can being. Control unit 124 may prevent a patient from starting a treatment too early if the temperature measured by the sensor 142 has not yet reached the threshold. In some instances, after reaching the threshold temperature, control unit 124 provides an indication or notification that the measured temperature has reached the threshold temperature. Moreover, in some embodiments, the control unit 124 may automatically start pump actuator 122 after the measured temperature has reached the threshold.

In some embodiments, the temperature sensor 142 may be in-line with the fluid tube 108*a*. During heating, the control unit 124 is configured to cause the pump actuator 122 to operate in forward and reverse one or more time to cause the fresh dialysis fluid in the container 104 to mix, thereby smoothing any temperature gradients. This mixing may also provide the in-line sensor 142 with a more accurate representation of the fluid temperature in the container 104. In yet further embodiments, the heater 140 may be an in-line heater.

The APD machine 100 of FIG. 6 also includes a power controller 610 and a power supply 612. The example power controller 610 is configured to regulate the power supply 612 for providing power to the control unit 124, the pump actuator 122, the control interface 604, the communication interface 606, the heater control 608, the temperature sensor 142, and/or the heater 140. The power controller 610 may also provide power for the pressure sensor 130 and/or the flow sensor 132. In other embodiments, the flow sensor 132 may have a self-contained battery and the pressure sensor 130 may not need power.

The power supply 612 includes, for example, one or more battery. In some embodiments, power supply 612 may be enclosed within the housing 202 illustrated in FIG. 2. Alternatively, power supply 612 may be provided in a pocket or held in place by a fastener of a clothing item or bag. Here, wires may be routed through the bag and/or clothing with connectors for the heater 140/heater control 608 and the control unit 124/pump actuator 122/control interface 604/communication interface 606.

The example power controller 610 is configured to measure a remaining energy level of the power supply 610, which is transmitted to the control unit 124. The control unit 124 may use the energy estimation for displaying a battery level indicator on the control interface 604 and/or the application 622. Further, the control unit 124 may compare an estimated energy level to an amount of energy needed to heat the container 104 and/or operate the pump actuator 122 for a treatment cycle. If the amount of energy in the power supply 612 does not meet a power threshold, control unit 124 may provide an indication of a low power level. In some embodiments, the control unit 124 may prevent the treatment from beginning until, for example, the power supply is recharged to a certain level or the batteries are replaced. This prevention keeps the APD machine 100 from starting a treatment then running out of power as for example, the heater 140 is warming the container 104 or the pump actuator 122 is pumping fluid to/from the peritoneal cavity 106.

IV. APD MACHINE OPERATION EMBODIMENT

Figure 8:
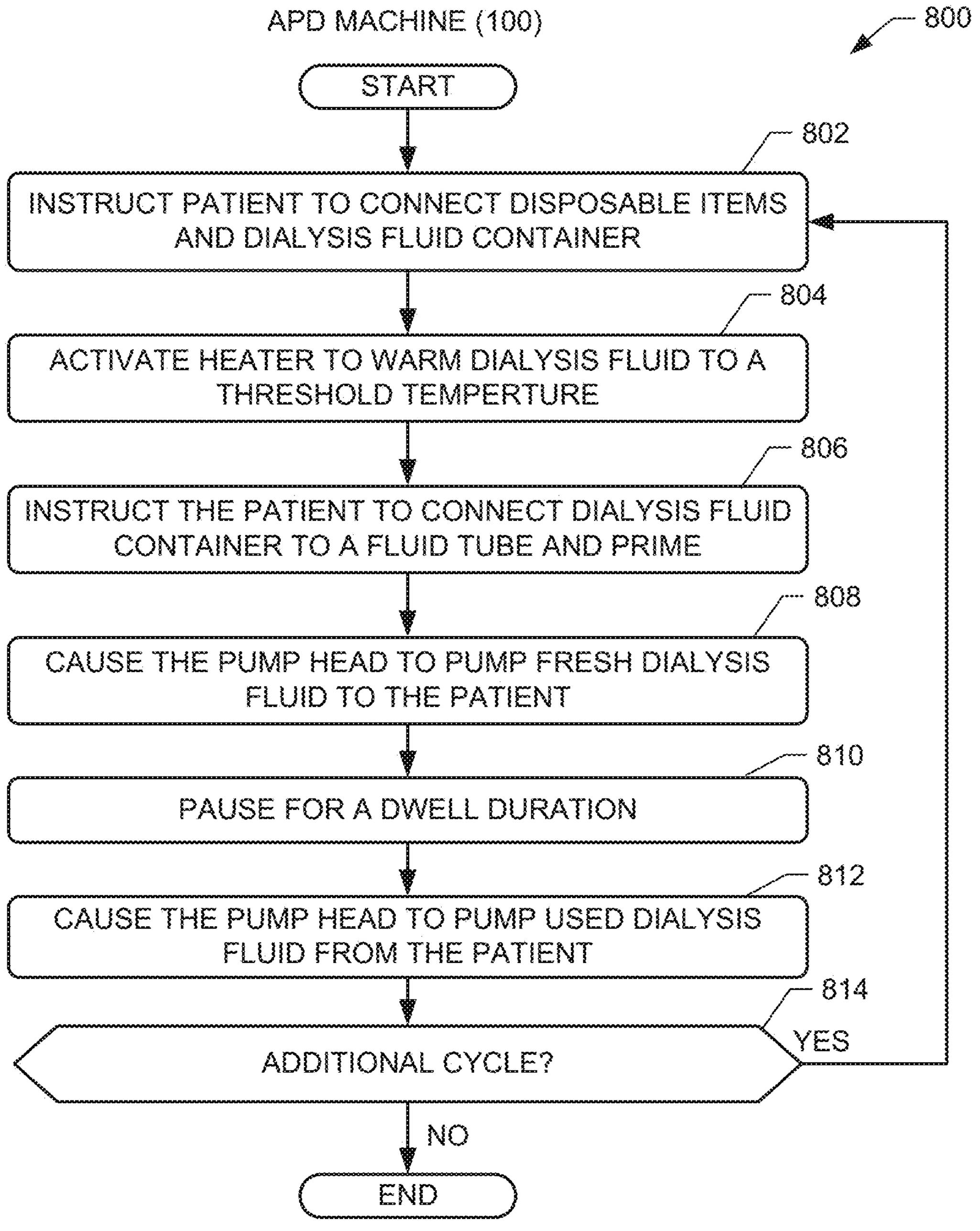
FIG. 8 is a flow diagram of an example procedure for operating the APD machine of FIGS. 1, 2 and 6, according to an example embodiment of the present disclosure.

FIG. 8 is a flow diagram of an example procedure 800 for operating the APD machine 100 of FIGS. 1, 2, and 6 for at least one cycle of a kidney failure therapy, according to an example embodiment of the present disclosure. Although the procedure 800 is described with reference to the flow diagram illustrated in FIG. 8, it should be appreciated that many other methods of performing the steps associated with the procedure 800 may be used. For example, the order of many of the blocks may be changed, certain blocks may be combined with other blocks, and many of the blocks described may be optional. In an embodiment, the number of blocks may be changed. For example, feedback steps can be added for controlling the pump actuator 122 using feedback from the temperature sensor 142, the pressure sensor 130, and/or the flow sensor 132. The actions described in the procedure 800 are specified by one or more instructions and may be performed among multiple devices including, for example, the control unit 124 and/or the heater control 608 and stored in the memory device 602 of FIG. 6.

The example procedure 800 begins when the control interface 604 and/or the application 622 on the user device 620 instructs the patient to connect disposable items together (block 802). This includes connecting the fluid tubes 108*a* and 108*b* to the pump head 120, and connect the sensors 130 and 132 in-line with the fluid tube 108*b*. This also includes instructing the patient to place the dialysis fluid container 104 in the clothing or bag/pouch such that the port 110 is in a downward position. This step may further include the patient making electrical connections between the heater 140, the control unit 124, and the power supply 612. In some instances, the patient may perform these steps without instruction from the control unit 124.

Next, the heater 140 warms fresh dialysis fluid within the dialysis fluid container (block 804). In some instances, heater 140 is activated by the patient using a heater control 608. In other instances, the patient uses the control interface 604 to cause the heater 140 to activate. The heater 140 warms the dialysis fluid container 140 for a set time, until a threshold temperature is reached, and/or until the indicator 144 provides an indication that the temperature has reached a threshold, causing the patient to turn off the heater 140.

After warming, the control interface 604 and/or the application 622 on the user device 620 instructs the patient to connect the fluid tube 108*a* to the port 110 of the container 110 (block 806). In some embodiments, the port 110 includes an end cap that enables the patient to break a seal on the container 110. The control interface 604 and/or the application 622 on the user device 620 instructs the patient to prime the flowpath of the fluid tubes 108*a* and 108*b* until at least some fluid exits a second side of the fluid tube 108*b* that connects to the catheter 116. During this time, the patient may engage the control interface 604 to cause the control unit 124 to cause the pump actuator 122 to move the pump head 120 for a priming operation, where fluid is pumped until a certain volume passes through the flow sensor 132. After priming, the control interface 604 and/or the application 622 on the user device 620 instructs the patient to connect the second end of the fluid tube 108*b* to the catheter 116 to complete the fluid flowpath.

In some embodiments, the priming operation may be performed before heating. In these embodiments, the control interface 604 and/or the application 622 on the user device 620 instructs the patient to break the seal on the container 104 and prime the fluid tubes 108*a* and 108*b*. The control unit 124 may cause the pump head 120 to occlude the fresh dialysis fluid during the warming step until the threshold temperature is reached.

The example procedure 800 continues by the control unit 124 causes the pump head 120 to pump the fresh dialysis fluid from the container 104 to the peritoneal cavity 106 (block 808). In some embodiments, the control unit 124 begins treatment setup after receiving a start command from a patient via the control interface 604. The control unit 124 may cause, or example, 200 mL of fresh dialysis fluid to be pumped at a rate of 50 mL/min to eliminate or reduce patient discomfort associated with having their peritoneal cavity 106 filled. After detecting that 200 mL of fluid has been pumped, the control unit 124 increases the flow rate to, for example, 200 mL/min for the remainder of the fill phase and/or until the container 104 is emptied.

After the fill phase, the control unit 124 pauses or switches off for a dwell duration (block 810). The dwell duration may be entered by the patient via the control interface 604 or specified by a treatment parameter. During this dwell duration, the rollers 302 of the pump head 120 may operate as a valve to prevent backflow from the peritoneal cavity 106. After the dwell duration, the control unit 128 may activate an alarm or provide an indication for patient to activate a drain phase (block 812). In other embodiments, the control unit 124 automatically begins the drain phase after an expiration of the dwell duration, with an option for a patient to pause the pumping. During this drain phase, the control unit 124 causes the pump actuator 122 to rotate the pump head 120 in a reverse direction to pump used dialysis fluid from the peritoneal cavity 106 back into the container 104. The control unit 124 may cause the pump actuator 122 to operate for a specified time duration and/or until no further fluid is detected via the flow sensor 132.

The control unit 124 may then end the cycle of treatment and determine if another cycle is to be performed according to a prescription or a plan (block 814). If another cycle is to be performed, the control interface 604 and/or the application 622 on the user device 620 instructs the patient to replace the disposable items for another cycle (block 802). If another cycle is not to be performed, the example procedure 800 ends.

V. CLOTHING EMBODIMENT

Figure 9:
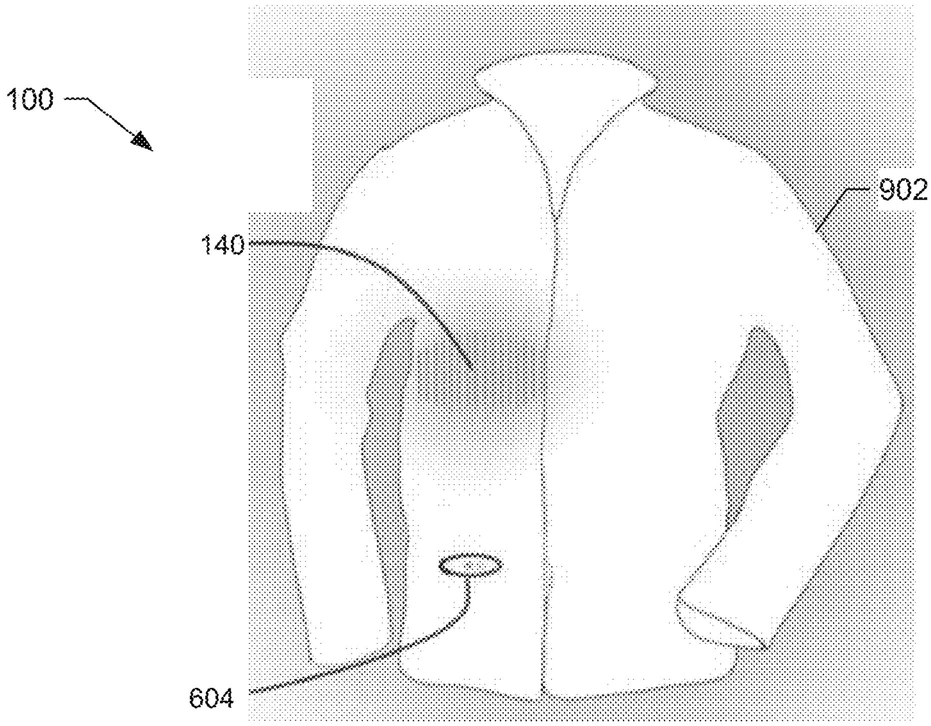
FIGS. 9 to 12 are diagrams of the APD machine of FIGS. 1, 2, and 6 integrated into articles of clothing, according to example embodiments of the present disclosure.

FIG. 9 illustrates APD machine 100 of FIGS. 1, 2, and 6 integrated into an article of clothing 902, according to example embodiments of the present disclosure. In the illustrated example, clothing 902 includes a shirt. In other examples, the clothing may include at least one of a jacket, a coat, a shirt, a sweater, a tunic, or pants. From the outside, as illustrated in FIG. 9, the APD machine 100 is not readily visible. This enables a patient to discretely perform a peritoneal exchange while located outside their home. The only visible portion of the APD machine 100 includes, for example, control interface 604, shown as colored indicators that represent a status of the kidney failure therapy or of the pump head 120/pump actuator 122. In some instances, the illustrated control interface 604 may include one or more button for starting/stopping the pump actuator 122.

Figure 10:
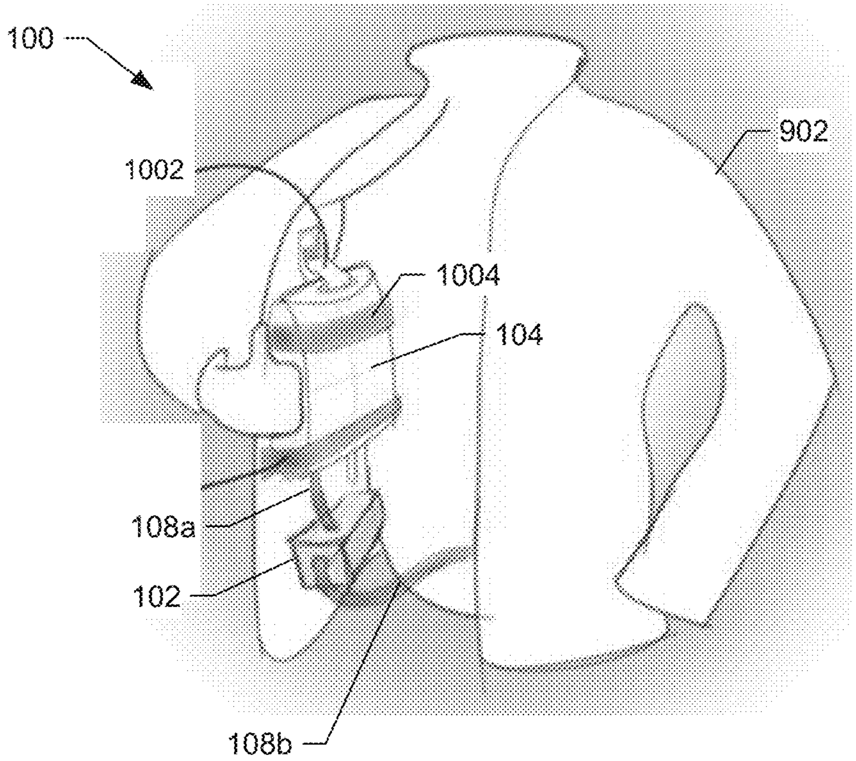

FIG. 9 also shows a heater 140 provided in a front section of the clothing 902. Heater 140 may be located internally within the clothing 902 adjacent to a location for a dialysis fluid container 104. FIG. 10 illustrated APD machine 100 of FIGS. 1, 2, and 6 having a side of the article of clothing 902 opened. As illustrated, the clothing includes a fastener 1002 (or hook) and at least one elastic strap 1004 for holding the dialysis container 104 in place adjacent to the heater 140. The fastener 1002 may also help position the dialysis container 104 such that an output port faces downward, which enables air bubbles to settle in a top of the container 104 away from the port. In other examples the fastener 1002 and/or the strap 1004 may be replaced by a pocket or other section of the clothing 902.

In the illustrated embodiment, the delivery system 102 is aligned with the control interface 604 shown on the outside of the clothing 902 in FIG. 9. Additionally, FIG. 10 shows that delivery system 102 may be easily connected to the dialysis fluid container 104 via a fluid tube 108*a* and connected to a patient's catheter via fluid tube 108*b*. The compactness of the delivery system 102 and the container 104 reduce the length of fluid tubing needed, thereby reducing a potential hindrance on the patient. As further illustrated, delivery system 102 and container 104 have a relatively low profile and weight, thereby enabling discrete mobility.

Figure 11:
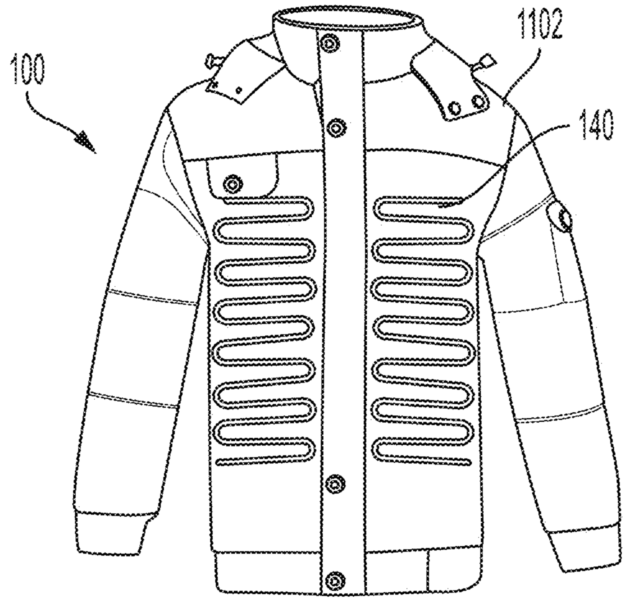
Figure 12:
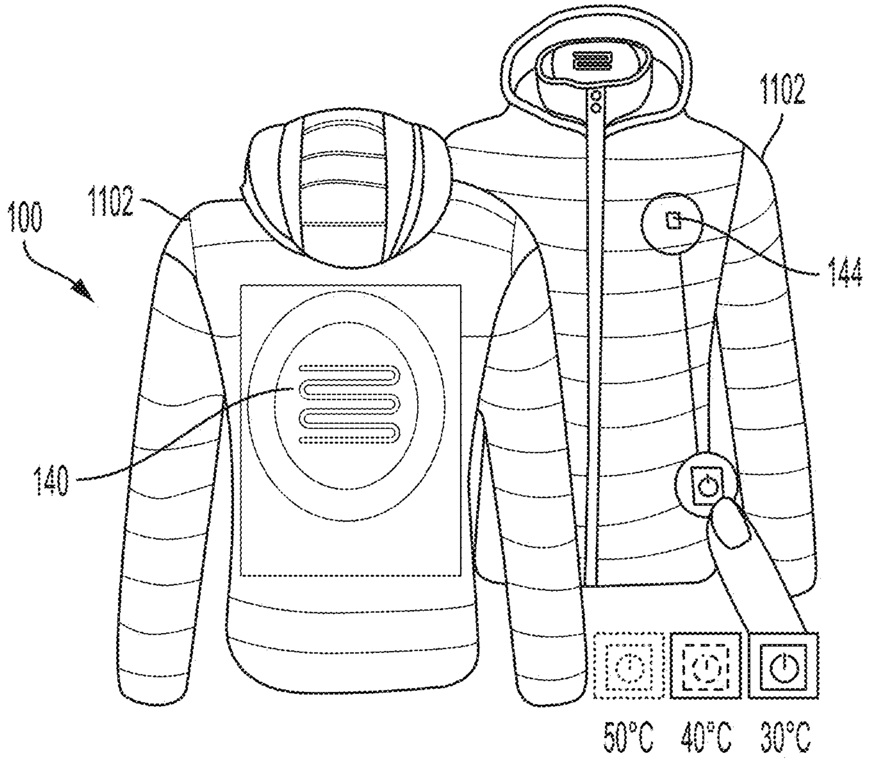

FIGS. 11 and 12 are diagrams of another article of clothing 1102 containing the APD machine 100 of FIGS. 1, 2, and 6, according to an example embodiment of the present disclosure. As illustrated, clothing 1102 includes a winter coat. FIG. 11 shows that the heater 140 may include heating coils and be located in a front of the clothing 1102. FIG. 12 shows that the heater 140 may include a heading pad and be located in a back of the clothing 1102. FIG. 12 also shows an example of the indicator 144. In the illustrated example, the indicator 144 changes color based on a detected temperature of a dialysis fluid container (or an interior temperature of the clothing 1102). A patient may readily ad discretely observe the temperature change to determine when fresh dialysis fluid is warmed sufficiently to being a kidney failure therapy.

In some embodiments, the use of a winter coat may support dermo-dialysis, where sweat is used to remove waste from a patient. The winter coat in conjunction with a heater may cause a patient to sweat for an extended period of time, thereby increasing the amount of toxins removed from their body. In these embodiments, the heater may remain on for an extended duration to facilitate patient sweating.

VI. BAG/POUCH EMBODIMENT

Figure 13:
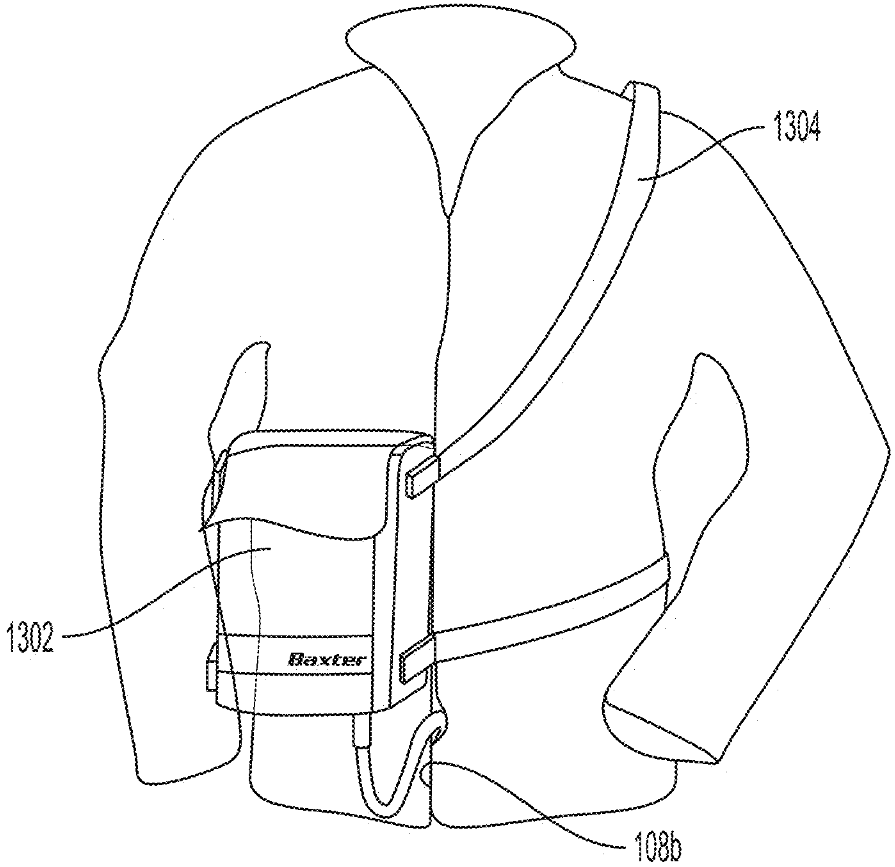
FIGS. 13 and 14 are diagrams showing the APD machine of FIGS. 1, 2 and 6 contained within a bag or pouch, according to example embodiments of the present disclosure.
Figure 14:
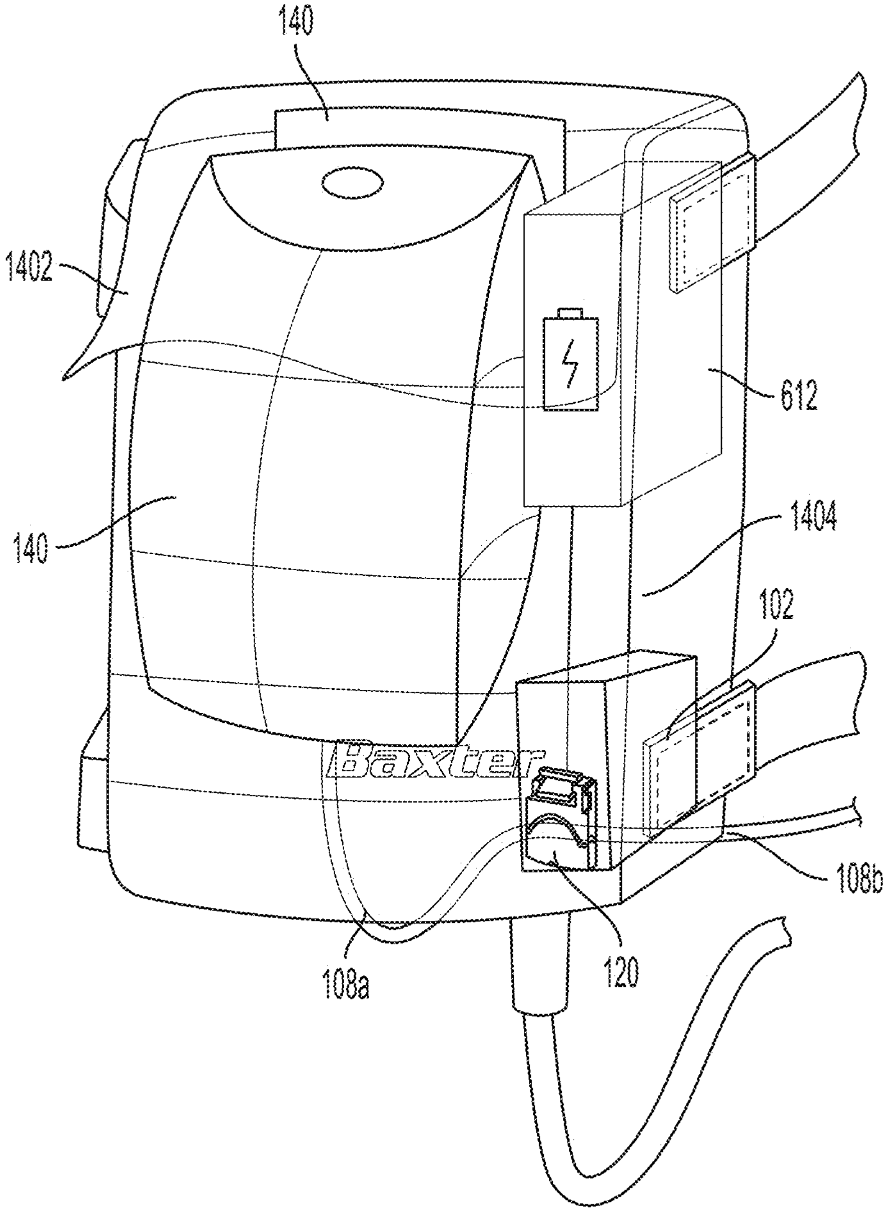

FIGS. 13 and 14 illustrate the APD machine 100 of FIGS. 1, 2, and 6 contained within a bag or pouch 1302, according to example embodiments of the present disclosure. As illustrated in FIG. 13, the bag or pouch 1302 is connected to an adjustable strap 1304 for securing the bag or pouch to the patient. Strap 1304 also provides support for the weight of the APD machine 100. In other examples, the bag or pouch may include a backpack.

The bag or pouch is placed on a front side of the patient to reduce a length of the fluid tube 108*b*, so as to not restrict patient movement. The reduced fluid tube length 108*b* also makes the system more discrete. Also, in some instances, the fluid tube 108*b* may be easily detachable from the APD machine 100 to enable the patient to remove the bag 1302 during a dwell duration.

FIG. 14 shows that the bag or pouch 1302 includes front pocket or section 1402 for holding the dialysis fluid container 104. The front pocket or section 1402 is placed adjacent to or in proximity to the heater 140 (which includes a heating pad) for warming fresh dialysis fluid within the container 104. In some embodiments, only a single pocket or section is provided for the container 104 and the APD machine 100.

The bag or pouch 1302 also includes a power supply 612, which may include a battery pack. The power supply 612 may be secured in place via a pocket, fastener, strap, or section. Internal wiring may electrically couple the power supply 612 to the heater 140, without needing connection by the patient. The bag or pouch 1302 further includes the delivery system 102, which may be located in or secured by another pocket, fastener, strap or section 1404. The delivery system 102 may be electrically connected to the power supply 612 via wires that are internal to the bag or pouch 1302, thereby eliminating need of connection by the patient.

As shown FIG. 14, the fluid tubes 108*a* and 108*b* are easily connectable to the pump head 120 of the delivery system 102. In this embodiment, the sensors 130 and 132 may be integrated into a housing of the delivery system 102. Alternatively, the sensors 130 and 132 may be connectable to the fluid tube 108*b*.

In the illustrated example, the bag or pouch 1302 may weigh less than one kilogram, not taking into account the weight of the dialysis fluid. This enables the bag or pouch with the APD machine 100 to be worn easily by a patient outside their homes. Further, the use of lower weight components reduces typical noises and vibrations associated with standard APD machines, thereby making it easier for patient wear. Reducing the amount of time a patient is confined to a bed or chair for dialysis accordingly improves their quality of life and increases the chances that a patient will adhere to their dialysis schedule or prescription.

VII. CONCLUSION

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An automated peritoneal dialysis ("APD") apparatus comprising:
- a dialysis fluid container;
- a delivery system fluidly connected to the dialysis fluid container including:
  - a pump configured to pump fresh dialysis fluid from the dialysis fluid container to a peritoneal cavity of a patient, and to pump used dialysis fluid from the peritoneal cavity of the patient to the dialysis fluid container,
  - a pressure sensor configured to measure a pressure of the fresh and used dialysis fluid, and
  - a control unit configured to control the pump using the pressure measured by the pressure sensor; and
- a clothing item to be worn by the patient, the clothing item including
  - a first fastener or pocket sized to retain the dialysis fluid container,
  - a heating element positioned adjacent to the first fastener or the pocket for warming the fresh dialysis fluid in the dialysis fluid container, and
  - a second fastener or pocket sized to retain the delivery system.

2. The APD apparatus of claim 1, further comprising a temperature sensor positioned and arranged to measure a temperature of the fresh dialysis fluid.

3. The APD apparatus of claim 2, wherein the temperature sensor is located within the delivery system and is communicatively coupled to the control unit, and wherein the control unit is configured to cause the fresh dialysis fluid to be pumped to the patient after a temperature measured by the temperature sensor has reached a threshold temperature.

4. The APD apparatus of claim 2, wherein the temperature sensor is provided with the heating element, and wherein the clothing includes an indicator that is indicative of a temperature measured by the temperature sensor.

5. The APD apparatus of claim 4, wherein the indicator includes at least one of a light emitting device or thermochromic ink or gel that changes color based on the measured temperature.

6. The APD apparatus of claim 1, wherein the delivery system further includes a control interface communicatively coupled to the control unit, the control interface including a first control input to enable the patient to start the pump and a second control input to enable the patient to set a dwell time.

7. The APD apparatus of claim 6, wherein the control unit is configured to detect at least one event selected from a line occlusion, a fluid leak, a patient empty condition, or a law battery condition, and wherein the control interface is configured to provide an indication of the detected event.

8. The APD apparatus of claim 1, further comprising a power source for the control unit and the heating element, the power source provided with or stored in at least one of the control unit, the first fastener or pocket, or the second fastener or pocket.

9. The APD apparatus of claim 1, further comprising a power source located in a third fastener or pocket that has an electrical connection to the heating element for connection to the control unit.

10. The APD apparatus of claim 1, wherein a flow sensor and the pressure sensor are located between the pump and a catheter.

11. The APD apparatus of claim 10, wherein at least one of (i) the flow sensor includes at least one of a non-contact flow sensor or a disposable fluid flow rate sensor, or (ii) the pressure sensor includes at least one of a non-contact pressure sensor or a disposable pressure pod.

12. The APD apparatus of claim 1, wherein the pump includes at least one of a linear pump for operation on disposable fluid tubing or a rotary peristaltic pump having a disposable pump head.

13. The APD apparatus of claim 1, wherein the clothing item includes at least one of a jacket, a coat, a skirt, a sweater, a tunic, or pants.

14. The APD apparatus of claim 1, wherein the dialysis fluid container is a first dialysis fluid container, and wherein the control unit is configured to provide a first cycle or exchange pass of a peritoneal dialysis therapy for the first dialysis fluid container connected to the pump.

15. The APD apparatus of claim 14, wherein after the first cycle or exchange pass of the peritoneal dialysis therapy, the first dialysis fluid container is replaced with a second dialysis fluid container, and wherein the control unit is configured to provide a second cycle or exchange pass of the peritoneal dialysis therapy for the second dialysis fluid container connected to the pump.

16. The APD apparatus of claim 1, further comprising a flow sensor configured to measure a flow rate of the fresh and used dialysis fluid,
- wherein the control unit is configured to control the pump using the flow rate measured by the flow sensor and the pressure measured by the pressure sensor.

* * * * *